United States Patent
Berthold

(10) Patent No.: US 7,279,178 B1
(45) Date of Patent: Oct. 9, 2007

(54) THERAPEUTIC SYSTEM CONTAINING AN ACTIVE SUBSTANCE FOR THE APPLICATION ON THE SKIN WHICH CONTAINS AT LEAST TWO POLYMEROUS LAYERS

(75) Inventor: Achim Berthold, Darmstadt (DE)

(73) Assignee: LTS Lohmann Therapie-Systems AG, Andernach (DE)

( * ) Notice: Subject to any disclaimer, the term of this patent is extended or adjusted under 35 U.S.C. 154(b) by 205 days.

(21) Appl. No.: 09/830,300

(22) PCT Filed: Aug. 14, 2000

(86) PCT No.: PCT/EP00/07900

§ 371 (c)(1),
(2), (4) Date: Jul. 5, 2001

(87) PCT Pub. No.: WO01/13899

PCT Pub. Date: Mar. 1, 2001

(30) Foreign Application Priority Data

Aug. 25, 1999 (DE) ................ 199 40 238

(51) Int. Cl.
*A61F 13/00* (2006.01)
*A61K 9/70* (2006.01)
*A61K 9/32* (2006.01)

(52) U.S. Cl. .................. 424/449; 424/443; 424/484

(58) Field of Classification Search ................ 424/443, 424/447, 448, 449, 484–488; 514/964
See application file for complete search history.

(56) References Cited

U.S. PATENT DOCUMENTS

| 4,661,104 A | 4/1987 | von Bittera et al. |
| 5,023,084 A * | 6/1991 | Chien et al. ................. 424/448 |
| 5,151,271 A * | 9/1992 | Otsuka et al. ............... 424/443 |
| 5,186,938 A | 2/1993 | Sablotsky et al. |
| 5,306,503 A | 4/1994 | Müller et al. |
| 5,580,573 A * | 12/1996 | Kydonieus et al. ......... 424/449 |
| 6,063,838 A * | 5/2000 | Patnode et al. ............. 523/172 |
| 6,416,858 B1 * | 7/2002 | Ercillo et al. ............... 428/345 |

FOREIGN PATENT DOCUMENTS

| DE | 32 00 369 A1 | 8/1982 |
| DE | 35 25 767 A1 | 1/1987 |
| DE | 198 04 604 A1 | 8/1999 |
| EP | 0 464 573 A1 | 5/1975 |
| EP | 0 856 311 A1 | 8/1998 |
| WO | 86/00814 | 2/1986 |
| WO | WO96/22084 | 7/1996 |

\* cited by examiner

*Primary Examiner*—Sharmila G. Landau
(74) *Attorney, Agent, or Firm*—D. Peter Hochberg; Sean Mellino

(57) ABSTRACT

Active substance-containing therapeutic system for application on the skin, comprising at least two polymer-containing layers, characterized in that the polymers used for the different layers differ in their glass transition temperature (see FIG. 1).

11 Claims, 1 Drawing Sheet

THERAPEUTIC SYSTEM CONTAINING AN ACTIVE SUBSTANCE FOR THE APPLICATION ON THE SKIN WHICH CONTAINS AT LEAST TWO POLYMEROUS LAYERS

BACKGROUND OF THE INVENTION

1. Field of the Invention

The invention relates to an active substance-containing therapeutic system for application to the skin comprising at least two polymer-containing layers. The invention further relates to a manufacturing process as well as to a use of the therapeutic system.

2. Description of the Prior Art

The pharmaceutical preparation for delivery of active substances to the skin aims either at a transdermal systemic action or at a dermal, local action of the active substances released. Adherence to the application surface is secured through adhesives forming high-viscous, permanent-adhesive structures. Here, quality characteristics such as initial tackiness (tack), adhesive power (adhesion) and internal strength of the pressure-sensitive adhesive (cohesion) are distinguished.

The pharmaceutical preparation is an active substance-containing device which releases one or more medicinal agents at a predeterminable rate, continuously, over a defined period of time, to a defined site. Such a device is characterized by an exact plan of treatment, called dosage plan, and is called a therapeutic system (TS). As the systems according to the present invention are stuck to the skin as patches to obtain either a systemic or a local effect, these systems are referred to in the given context as transdermal therapeutic systems (TTSs) or as dermal therapeutic systems (DTSs).

The preparation according to the present invention has a high degree of efficacy. This means that the preparation leads to high bioavailability of the active substances. Action can be broken off at any time by the simple removal of the preparation. As a consequence, the preparation is characterized also by controllability of the active substance release. The preparation according to the invention furthermore has high reliability with regard to patients' observing the therapeutic plan (so-called compliance) since the frequency of application is greatly reduced as compared to conventional drug forms, and side effects occur only rarely. Further, the amount of active substance to be applied can, as a rule, be reduced. Thus, dose-dependent side effects are likewise reduced or avoided. This results in increased therapeutic safety.

Usually, an active substance-containing system, TTS or DTS, comprises an assembly of a plurality of layers comprising at least one active substance- and/or auxiliary substance-containing reservoir layer, a backing layer impermeable to the ingredients of the latter, and a protective layer to be removed prior to application to the skin.

The reservoir layer here consists as a rule of an amorphous polymer containing active substances and/or auxiliary substances. Apart from a number of advantageous properties of the polymer, especially with regard to its use as patches, such as diffusion-dependent absorption or release of the ingredients, or their flexibility in conforming to a given shape of the body at the application site, amorphous polymers on the other hand tend to show cold flow in the patch, especially in the case of prolonged storage, as a consequence of comparatively insufficient cohesion.

Whereas in pure-crystalline substances, at the melting point the molecular motion increases rapidly from a relatively low level to a high level with increasing temperature, amorphous polymers such as adhesives behave differently.

As the temperature increases, molecular movement increases in several reversible stages, mostly 5 different ones. In detail, five ranges of viscoelasticity are distinguished as glassy state (hard; lowest temperature), leathery state (turning point=glass transition temperature ($T_g$)=temperature at which a polymer changes from the solid glassy state to the rubber-elastic state), rubber-elastic state, rubber-elastic flow, and viscous state (highest temperature).

The transition from glassy state to the rubber-like state is accompanied by a marked change in the physical properties such as specific volume, modulus of elasticity, heat capacity, thermomechanic properties and refractive index. The melting point ($T_m$; solid and liquid polymer are balanced) of amorphous polymers is defined by partially crystalline polymer regions. Here, $T_g$ is always below $T_m$.

Distinctions are made between:

Polymers which at room temperature ($T_A$) are in the solid glassy state, with $T_g$, $T_M > T_a$. Examples are isotactic polystyrene: $T_g = 85°$ C./$T_m = 240°$ C.; polyethylene terephthalate: $T_g = 69°$ C./$T_m = 265°$ C.; polyhexamethylene adipamide: $T_g = 53°$ C./$T_m = 265°$ C.; polytetrafluoroethylene: $T_g = 126°$ C./$T_m = 325°$ C.). Polymers which are in the soft rubberlike intermediate state ($T_m > T_a > T_g$). Examples are high-density polyethylene: $T_g = -70°$ C./$T_m = 139°$ C.; isotactic polypropylene: $T_g = -18°$ C./$T_m = 186°$ C. Polymers which are in the liquid viscous state ($T_a > T_m$, $T_g$; examples are polydimethyl siloxane: $T_g = -121°$ C./$T_m = -40°$ C.; 1,4-cis-polybutadiene: $T_g = -95°$ C./$T_m = 2°$ C.).

It can be derived from this that the cohesion and thereby the cold flow of an adhesive having high-viscous, permanent-adhesive polymer structures is decisively influenced by the glass transition temperature of the polymers employed.

Cold flow describes a property of a material. The materials affected by this start to flow during storage without having been subjected to special influences, consequently they can be considered high-viscous liquids.

It is known from practice that TTSs and DTSs often tend to show cold flow. This leads to a patch becoming agglutinated with the primary packing means while it is being stored so that it can be removed subsequently only with difficulty. A further problem consists in that after application the patches leave black margins, residues of adhesive, on the surface of application which in part can be removed only by means of intensive cleaning measures.

WO 86/00814 as well as U.S. Pat. No. 5,186,938 describe the possibility of improving the cold flow in glycerol trinitrate-containing, self-adhesive, polyacrylic acid-derived polymers by crosslinking the polymers. For crosslinking, divalent metal ions or melamine are used, for example. This creates a coherent network that has a considerably lower tendency for cold flow than the starting polymer. Crosslinkage, which has a positive effect on cohesion, has, on the other hand, a negative influence on tack, which thereby deteriorates.

The latter is a universal rule of thumb. The inventors of the known method attempt to solve the problem by using the agent that brings about the cross linkage only in a relatively small amount in order to ensure a minimum tack. The problem with the procedure described by the inventors is that the degree of cross linkage must be adjusted accurately to guarantee optimum system properties.

To be independent from the sensitivity of cohesion and tack, which is dependent on the degree of cross link, a different procedure is proposed in EP 0 856 311 A1 and DE 197 06 824 C1. To improve the cohesion of the matrix without reducing the adhesive power on the skin, systems are proposed which consist of at least two layers. The special aspect here is that the layers although having the same polymer composition and the same concentration of dissolved ingredients, differ in the degree of cross linkage. While a layer with a lower degree of cross link ensures adhesion to the skin, another layer, having a higher cross link degree, reduces cold flow. Cross-linking is carried through in a known manner, for example, by addition of metallic ions or reactive reagents as well as by electron irradiation or irradiation with ultraviolet light.

Another possibility to improve cohesion is known from DE 40 20 144 C2. This document describes a possibility of improving cold flow without the use of reagents for cross-linking. To this end, a further non-adhesive but film-forming polymer is added to the self-adhesive base polymer. This film-forming polymer, which is typically characterized by a high molecular weight, results in a considerable improvement of cohesion.

The above-described processes for improving cohesion cannot be employed in all cases. For example, not all polymers which are adhesive and are thus suitable for the production of self-adhesive TTSs or DTSs can be crosslinked. Also, admixture of cohesion-enhancing polymers is not always possible, for reasons of compatibility.

SUMMARY OF THE INVENTION

Starting from the aforementioned state of the art, it is the object of the invention to provide a process for improving cohesion in order to achieve a clear reduction of the cold flow, which process, at least for the most part, overcomes the difficulties and technical limits observed heretofore and leads to a high bioavailability of the active substances and auxiliary substances contained.

DESCRIPTION OF THE PREFERRED EMBODIMENT

Figure 1:
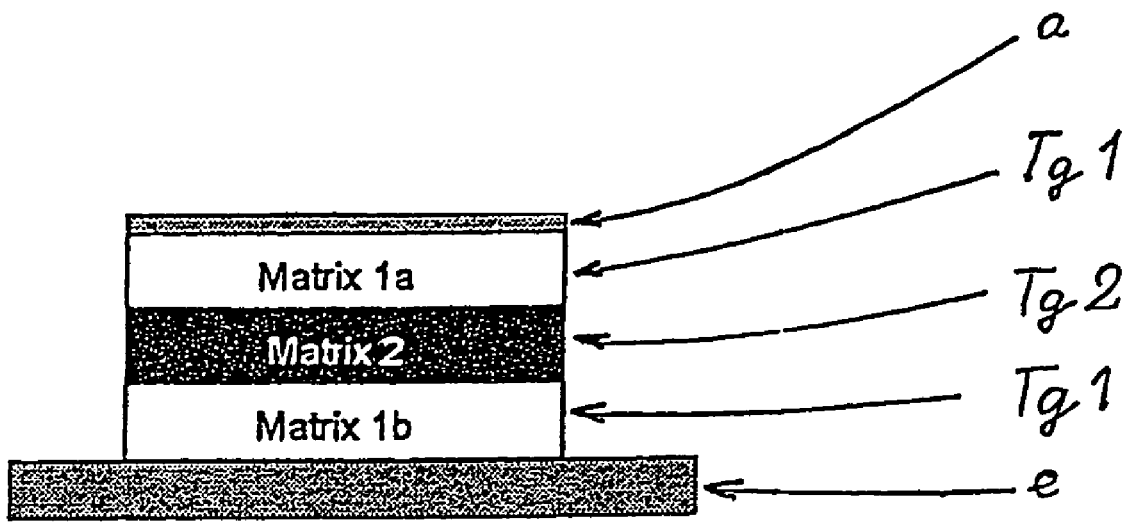
FIG. 1 is a cross-sectional view of a therapeutically active substance-containing therapeutic system in accordance with the present invention.

This object is achieved with an active substance-containing therapeutic system for application on the skin comprising at least two polymer-containing layers, by a layered structure of the TTS or DTS.

The various layers differ in their glass transition temperature (Tg). The layer(s) with the higher glass transition temperature(s) lead(s) to an improvement of the cohesion of the entire system. As a consequence, cold flow is reduced, so that the problem of TTSs or DTSs becoming agglutinated with the primary packaging means during storage and leaving black edges on the application surface owing to residues of adhesive does no longer appear or is strongly reduced. Furthermore, incompatibilities are avoided by the fact that the polymers used are present in different layers, so that their interaction is substantially restricted to the interfaces. In favourable cases one can dispense with cross-linking.

Further embodiments are described in accordance with the subclaims.

One of the layers can simultaneously be provided as a control means for active substance release.

The process according to the invention further provides for at least one of the layers to be formed and arranged as an active substance reservoir.

Finally, a process for the manufacture of the therapeutic system comprises the steps of laminating at least two polymer-containing layers upon one another, with the layers containing polymers which differ in their glass transition temperature.

A use of the therapeutic system according to the inventions serves the topical or transdermal release of active substances to the skin of an organism.

An exemplary, schematic representation of the system according to the invention can be seen from FIG. 1.

This shows an embodiment example consisting of five layers (a to e). The layers are:

a) backing layer, b) matrix 1$a$ with a polymer designated as Tg1, c) matrix 2 with a polymer designated as Tg2, d) matrix 1$b$ with a polymer designated as Tg1, e) protective layer, detachable, with Tg2>Tg1.

EXAMPLE

To prepare the matrix 1$a$, 25.0 g of a polymer based on methacrylic acid (Eudragit® L100) are dissolved in 16.1 g of ethanol. After complete dissolution of the methacrylic acid polymer, to this pre-solution were added the active substances estradiol (925.0 mg) and norethisterone acetate (5.25 g), and this was again stirred until the active substances were dissolved. Thereafter, 38.84 g of an adhesive solution (solution of a self-adhesive polymer based on polyacrylic acid esters in ethyl acetate, 51.0% wt.; Durotak® 387-2287), 11.50 g of a tack-imparting resin (Hercolyn® D), 7.5 g of glycerine, as well as 6.0 g of a solution of aluminium acetyl acetonate in ethyl acetate (4%-wt.) were successively added and subsequently homogenised. The resultant mass had a solids content of 45%-wt. This mass was then applied to a siliconized polyester film (Hostaphan® RN100) by means of a film casting instrument, at a layer thickness of 250 µm, and dried under defined conditions (30 min at 50° C.). The dried film was covered with a flexible polyester film (Hostaphan® RN15), which represented the later backing layer. Matrix 1$b$ was prepared in an analogous manner, with the difference that the final covering with a flexible polyester film was left out. To prepare matrix 2, 30.0 g of a high-molecular polymer based on methacrylic acid ester (Plastoid® B) in ethyl acetate were initially dissolved in ethyl acetate, so that a 30%-wt. solution resulted. This solution was then applied to a siliconized polyester film (Hostaphan® RN100) by means of a film casting instrument, at a layer thickness of 250 µm, and dried under defined conditions (30 min at 50° C.).

When the dried matrices had been obtained, the siliconized polyester film was removed from matrix 1$a$ and the matrix laminated on matrix 2. Then, the siliconized polyester film was removed from matrix 2 and the matrix laminated with matrix 1$b$. The result was a system comprising the layers: a) backing layer (Hostaphan® RN15), b) matrix 1$a$, c) matrix 2, d) matrix 1$b$, and e) protective layer (Hostaphan® RN100). The system is schematically shown in FIG. 1.

To assess the cold flow, the mentioned formulations and a formulation which contained only the matrices 1$a$ and 1$b$ were stored under defined conditions (40° C., 75% relative humidity). The laminate without matrix 2 showed strong cold flow already after one month. By contrast, such cold flow was not observed in the laminate comprising matrix 2.

The invention has been described with particular emphasis on the preferred embodiments, but variations and modifications within the spirit and scope of the invention may occur to those skilled in the art to which the invention pertains.

The invention claimed is:

1. A method for providing therapeutic applications in humane medicine, said method comprising the step of applying to living skin a therapeutically active substance-containing therapeutic system, the system comprising three polymer-containing layers, wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different, wherein at least one of said three polymer layers contains at least one therapeutically active substance and wherein said glass transition temperatures of said layers improve cohesion of said system for reducing cold flow in said system.

2. An active substance-containing therapeutic system for application on the skin, said system comprising three polymer-containing layers, wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different, wherein at least one of said three polymer layers contains at least one therapeutically active substance and wherein said glass transition temperatures of said layers improve cohesion of said system for reducing cold flow in said system.

3. The therapeutic system according to claim 2, wherein said system further comprises a backing layer and a protective layer.

4. The therapeutic system according to claim 2, wherein at least one of said polymer-containing layers comprises a high-molecular weight polymer having film-forming properties.

5. The therapeutic system according to claim 2, wherein at least one of said polymer-containing layers is formed and arranged as an active substance reservoir.

6. The therapeutic system according to claim 2, wherein at least one of said polymer-containing layers is formed to simultaneously serve as a control means for active substance release.

7. A process for manufacturing a therapeutic system according to claim 2, said process comprising the steps of laminating a first layer which comprises a polymer having a glass transition temperature ($T_g1$) onto a second layer for reducing cold flow in said system, said second layer comprising a polymer having a glass transition temperature ($T_g2$), and subsequently laminating a third layer on said second layer, said third layer having a polymer having a glass transition temperature ($T_g3$), wherein $T_g2$ is greater than $T_g1$ and $T_g3$, and the glass transition temperature $T_g1$ of the polymer of said first layer and the glass transition temperature $T_g3$ of the polymer of said third layer are identical or different, wherein at least one therapeutically active substance is added to at least one of said layers and wherein said glass transition temperatures of said layers improve cohesion of said system for reducing cold flow in said system.

8. A method for providing therapeutic applications in humane medicine, said method comprising the step of applying to living skin a therapeutically active substance-containing therapeutic system, the system comprising three polymer-containing layers, wherein at least one of said polymer-containing layers is an active substance release rate-controlling layer, and wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different, wherein at least one of said three polymer layers contains at least one therapeutically active substance and wherein said glass transition temperatures of said layers improve cohesion of said system for reducing cold flow in said system.

9. A method for providing therapeutic applications in humane medicine, said method comprising the step of applying to living skin a therapeutically active substance-containing therapeutic system, the system comprising three polymer-containing layers, wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different; and wherein said polymer having a glass transition temperature ($T_g1$) and said polymer having a glass transition temperature ($T_g2$) are selected from the group consisting of polymers based on methacrylic acid and polymers based on polyacrylic acid esters, and said polymer having a glass transition temperature ($T_g3$) is selected from the group consisting of methacrylic acid esters; and wherein at least one of said three polymer layers contains at least one therapeutically active substance and wherein said glass transition temperatures of said layers improve cohesion of said system for reducing cold flow in said system.

10. An active substance-containing therapeutic system for application on the skin, said system comprising three polymer-containing layers, wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different; and wherein said polymer having a glass transition temperature ($T_g1$) and said polymer having a glass transition temperature ($T_g2$) are selected from the group consisting of polymers based on methacrylic acid and polymers based on polyacrylic acid esters, and said polymer having a glass transition temperature ($T_g3$) is selected from the group consisting of methacrylic acid esters; and wherein at least one of said three polymer layers contains at least one therapeutically active substance and wherein said glass transition temperatures of said layers improve cohesion of said system for reducing cold flow in said system.

11. A method for providing therapeutic applications in humane medicine, said method comprising the step of applying to living skin a therapeutically active substance-containing therapeutic system, the system comprising three polymer-containing layers, wherein at least one of said polymer-containing layers is an active substance release rate-controlling layer, and wherein;

a first layer comprises a polymer having a glass transition temperature ($T_g1$), a second layer comprises a polymer having a glass transition temperature ($T_g2$), and a third layer comprises a polymer having a glass transition temperature ($T_g3$), said first, second and third layers being laminated on top of each other such that said second layer is located between said first layer and said third layer and is directly connected to the first layer and to the third layer; and wherein $T_g2$ is greater than $T_g1$ and $T_g3$, and the glass transition temperature $T_g1$ of the polymer of said first layer and the glass transition temperature $T_g3$ of the polymer of said third layer are identical or different; and wherein said polymer having a glass transition temperature ($T_g1$) and said polymer having a glass transition temperature ($T_g2$) are selected from the group consisting of polymers based on methacrylic acid and polymers based on polyacrylic acid esters, and said polymer having a glass transition temperature ($T_g3$) is selected from the group consisting of methacrylic acid esters; and wherein at least one of said three polymer layers contains at least one therapeutically active substance and wherein said glass transition temperatures of said layers improve cohesion of said system for reducing cold flow in said system.

\* \* \* \* \*